United States Patent
Chen et al.

(10) Patent No.: US 10,544,129 B2
(45) Date of Patent: Jan. 28, 2020

(54) CRYSTALLINE FORMS OF AP26113, AND PREPARATION METHOD THEREOF

(71) Applicant: Crystal Pharmatech Co., Ltd., Suzhou, Jiangsu (CN)

(72) Inventors: Minhua Chen, Suzhou (CN); Yanfeng Zhang, Suzhou (CN); Jinqiu Wang, Suzhou (CN); Kai Liu, Suzhou (CN); Xiaoyu Zhang, Suzhou (CN)

(73) Assignee: Crystal Pharmatech Co., Ltd., Suzhou (CN)

( * ) Notice: Subject to any disclaimer, the term of this patent is extended or adjusted under 35 U.S.C. 154(b) by 0 days.

(21) Appl. No.: 16/344,443

(22) PCT Filed: Oct. 25, 2017

(86) PCT No.: PCT/CN2017/107652
§ 371 (c)(1),
(2) Date: Apr. 24, 2019

(87) PCT Pub. No.: WO2018/077187
PCT Pub. Date: May 3, 2018

(65) Prior Publication Data
US 2019/0322646 A1    Oct. 24, 2019

(30) Foreign Application Priority Data
Oct. 25, 2016    (CN) .......................... 2016 1 0933496

(51) Int. Cl.
*C07D 401/14*    (2006.01)
(52) U.S. Cl.
CPC ........ *C07D 401/14* (2013.01); *C07B 2200/13* (2013.01)
(58) Field of Classification Search
CPC .................................................. C07D 401/14
See application file for complete search history.

(56) References Cited

U.S. PATENT DOCUMENTS 9,611,283 B1    4/2017    Zhang et al.

FOREIGN PATENT DOCUMENTS

| CN | 102105150 A | 6/2011 |
|----|---|---|
| WO | 2016065028 A1 | 4/2016 |

OTHER PUBLICATIONS

Huang et al., Discovery of Brigatinib (AP26113), a Phosphine Oxide-Containing, Potent, Orally Active Inhibitor of Anaplastic Lymphoma Kinase. J Med Chem. May 26, 2016;59(10):4948-64.

*Primary Examiner* — Paul V Ward
(74) *Attorney, Agent, or Firm* — McCarter & English, LLP; Steven G. Davis; Wei Song

(57) ABSTRACT

The present disclosure relates to two novel crystalline forms of AP26113 and processes for preparation thereof. The crystalline form CS1 and crystalline form CS2 of the present disclosure have advantages in solubility and stability, are suitable for development, and provide a better choice for preparation of pharmaceutical compositions containing AP26113, which is of great significance for drug development.

14 Claims, 7 Drawing Sheets

CRYSTALLINE FORMS OF AP26113, AND PREPARATION METHOD THEREOF

CROSS-REFERENCE TO RELATED APPLICATIONS

This application is a U.S. national stage application of the PCT International Application No. PCT/CN2017/107652 filed on Oct. 25, 2017, which claims the benefit of foreign priority of Chinese patent application No. 201610933496.7 filed on Oct. 25, 2016. The entire contents of the aforementioned application are incorporated herein by reference.

TECHNICAL FIELD

The present disclosure relates to the field of pharmaceutical chemistry, particularly relates to novel crystalline forms of AP26113 and processes for preparation thereof.

BACKGROUND

According to *Cancer Facts & Figures. 2017* reported by the American Cancer Society, about 85% of lung cancers are non-small cell lung cancer (NSCLC), wherein 3%-5% of NSCLCs are anaplastic lymphoma kinase (ALK) positive.

Crizotinib is a drug for first-line treatment of ALK-positive NSCLC approved by the US Food and Drug Administration (FDA). The patients initially respond to crizotinib, while most patients develop drug resistance and relapse within 12 months. Therefore, more and more cancer patients need new and effective therapies for ALK positive cancer.

AP26113, also known as Brigatinib, is a targeted small molecule tyrosine kinase inhibitor developed by Ariad Pharmaceuticals Inc. for the treatment of patients with crizotinib-resistant ALK-positive NSCLC. The drug was designated as a breakthrough therapy by the FDA in August 2014 and was approved in the US on Apr. 28, 2017. Clinically, AP26113 has sustained anti-tumor activity in patients with ALK-positive NSCLC, including brain metastases patients. The chemical structure of AP26113 is shown in formula (I):

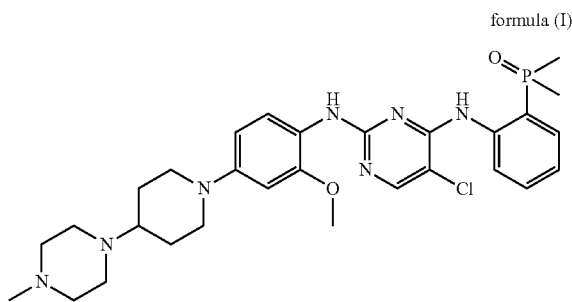

formula (I)

Different crystalline forms of drugs have different solubility and stability, which affect the absorption and bioavailability of drugs, leading to different clinical efficacy.

Patent application WO2016065028A1 reported crystalline forms of AP26113, including Form A, Form B, Form C, Form D, Form E, Form F, Form G, Form H, Form J, Form K and Form L, wherein Form J, Form K and Form L are mixed crystals containing Form A; Form E, Form F, Form G and Form H are solvates which are not suitable for direct pharmaceutical use; Form C and Form D are hydrates; Form B is an anhydrate. Form B, Form C and Form D convert to each other under different humidity conditions, wherein Form B easily absorbs moisture and transforms to a hydrate; Form C and Form D can be easily dehydrated and transform to other forms. Therefore, only Form A is relatively stable. However, inventors of the present disclosure found that Form A has low solubility and slow dissolution rate, which is not conducive to fast release and efficient use of drugs. Therefore, it is necessary to perform further polymorph screening on AP26113 to find crystalline forms that are more suitable for development.

The inventors of the present disclosure unexpectedly discovered two novel crystalline forms of AP26113 suitable for drug development after a large number of experiments, named as Form CS1 and Form CS2. Form CS1 and Form CS2 of AP26113 provided by the present disclosure have advantages in solubility, stability, hygroscopicity and processability, especially in terms of solubility, Form CS1 and Form CS2 have better solubility and dissolution rate than Form A of the prior art. The discovery of Form CS1 and Form CS2 of the present disclosure provides a better choice for the preparation of pharmaceutical compositions containing AP26113 and is of great significance for drug development.

SUMMARY

The main objective of the present disclosure is to provide novel crystalline forms of AP26113, processes for preparation and use thereof.

According to one objective of the present disclosure, crystalline form CS1 of AP26113 is provided (referred to as Form CS1). Without any limitation being implied, Form CS1 is a hydrate.

According to one aspect of the present disclosure, the X-ray powder diffraction pattern of Form CS1 shows characteristic peaks at 2theta values of 5.5°±0.2°, 21.6°±0.2° and 10.8°±0.2° using CuKα radiation.

Furthermore, the X-ray powder diffraction pattern of Form CS1 shows 1 or 2 or 3 characteristic peaks at 2theta values of 16.2°±0.2°, 21.0°±0.2° and 27.1°±0.2°. Preferably, the X-ray powder diffraction pattern of Form CS1 shows characteristic peaks at 2theta values of 16.2°±0.2°, 21.0°±0.2° and 27.1°±0.2.

Furthermore, the X-ray powder diffraction pattern of Form CS1 shows 1 or 2 or 3 characteristic peaks at 2theta values 8.5°±0.2°, 11.8°±0.2° and 18.6°±0.2°. Preferably, the X-ray powder diffraction pattern of Form CS1 shows characteristic peaks at 2theta values of 8.5°±0.2°, 11.8°±0.2° and 18.6°±0.2°.

In a preferred embodiment, the X-ray powder diffraction pattern of Form CS1 shows characteristic peaks at 2theta values of 5.5°±0.2°, 21.6°±0.2°, 10.8°±0.2°, 16.2°±0.2°, 21.0°±0.2°, 27.1°±0.2°, 8.5°±0.2°, 11.8°±0.2° and 18.6°±0.2°.

Without any limitation being implied, the X-ray powder diffraction pattern of Form CS1 is substantially as depicted in FIG. 1.

Another objective of the present disclosure is to provide a process for preparing Form CS1. The process comprises:
1) Dissolving AP26113 free base into a solvent mixture of alcohols and aromatic hydrocarbons, and then evaporating the solution at 30° C.-60° C. for 1-10 days to obtain Form CS1.
Or 2) Dissolving AP26113 free base in a solvent mixture of ethanol and aromatic hydrocarbons or a single solvent of water-saturated aromatic hydrocarbons, filtering and then stirring the filtrate at −20° C.-0° C. until solid precipitates. The obtained solid is Form CS1.

Or 3) Dissolving AP26113 free base in a solvent mixture of methanol and aromatic hydrocarbons, filtering and then stirring the filtrate at −20° C.-0° C. until solid precipitates, drying the obtained wet cake to get Form CS1.

In method 1):

Said alcohols are methanol, ethanol and isopropanol, preferably isopropanol.

Said aromatic hydrocarbon is toluene.

Said volume ratio of alcohol and aromatic hydrocarbon is from 1:4 to 1:2.

Said evaporation temperature is between 35° C.-50° C.

In method 2):

Said aromatic hydrocarbon is toluene.

Said volume ratio of ethanol and aromatic hydrocarbon is 1:4.

Said water-saturated aromatic hydrocarbon is water-saturated toluene.

In method 3):

Said aromatic hydrocarbon is toluene.

Said volume ratio of methanol and aromatic hydrocarbon is 1:9.

According to another objective of the present disclosure, crystalline form CS2 of AP26113 is provided (referred to as Form CS2). Without any limitation being implied, Form CS2 is a hydrate.

According to one aspect of the present disclosure, the X-ray powder diffraction pattern of Form CS2 shows characteristic peaks at 2theta values of 17.1°±0.2°, 22.9°±0.2° and 28.7°±0.2° using Cu-Kα radiation.

Furthermore, the X-ray powder diffraction pattern of Form CS2 shows 1 or 2 or 3 characteristic peaks at 2theta values of 27.3°±0.2°, 21.4°±0.2° and 5.7°±0.2°. Preferably, the X-ray powder diffraction pattern of Form CS2 shows characteristic peaks at 2theta values of 27.3°±0.2°, 21.4°±0.2° and 5.7°±0.2°.

Furthermore, the X-ray powder diffraction pattern of Form CS2 shows 1 or 2 or 3 characteristic peaks at 2theta values of 11.4°±0.2°, 8.7°±0.2° and 16.0°±0.2°. Preferably, the X-ray powder diffraction pattern of Form CS2 shows characteristic peaks at 2theta values of 11.4°±0.2°, 8.7°±0.2° and 16.0°±0.2°.

In a preferred embodiment, the X-ray powder diffraction pattern of Form CS2 shows characteristic peaks at 2theta values of 17.1°±0.2°, 22.9°±0.2°, 28.7°±0.2°, 27.3°±0.2°, 21.4°±0.2°, 5.7°±0.2°, 11.4°±0.2°, 8.7°±0.2° and 16.0°±0.2°.

Without any limitation being implied, the X-ray powder diffraction pattern of Form CS2 is substantially as depicted in FIG. 5.

Another objective of the present disclosure is to provide a process for preparing crystalline CS2. The process comprises:

1) Keeping the solid of Form CS1 under 30% RH-80% RH at room temperature for 1-30 days to get Form CS2.

Or 2) Dissolving AP26113 free base in a solvent mixture of alcohols and water, filtering and then stirring the filtrate at a temperature between −20° C.-0° C. until solid precipitates, keeping the obtained wet cake under 30% RH-75% RH at 25° C.-40° C. to get Form CS2.

In method 1):

Said humidity is 50% RH-80% RH;

Said keeping time is 5-16 days.

In method 2):

Said alcohol is methanol;

Said volume ratio of alcohol and water is 93:7 to 98:2;

Said keeping temperature is 35° C., said keeping humidity is 40% RH.

Said "room temperature" in the present disclosure is not an exact temperature value and refers to 10-30° C.

Said "evaporating" is accomplished by using a conventional method in the field. For example, slow evaporation is accomplished in a container covered by sealing film with pinholes. Rapid evaporation is accomplished in an open container.

Said "water-saturated toluene" is obtained by the following procedures. A certain amount of toluene and water are thoroughly mixed by shaking to obtain a toluene layer and an aqueous layer, and the toluene layer obtained is the "water-saturated toluene".

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CS1 and Form CS2 of the present disclosure are pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the numerical values and numerical ranges recited in the present disclosure are not to be construed as narrowly construed as a numerical value or a numerical range per se. It will be understood by those skilled in the art that they may vary depending on the specific technical environment without departing from the spirit of the disclosure. On the basis of the principle, there are fluctuations around specific numerical values. In the present disclosure, such a floating range which can be foreseen by those skilled in the art is often expressed by the term "about".

Furthermore, a pharmaceutical composition is provided; said pharmaceutical composition comprises a therapeutically effective amount of Form CS1 or Form CS2 or combinations thereof and pharmaceutically acceptable carriers, diluents or excipients.

Furthermore, Form CS1 or Form CS2 or combinations thereof can be used for preparing drugs inhibiting tyrosine kinase.

Furthermore, Form CS1 or Form CS2 or combinations thereof can be used for preparing drugs treating cancer, especially for preparing drugs treating ALK-positive NSCLC.

The advantageous effects of the present disclosure are:

At present, the crystalline form of AP26113 suitable for industrial production is rare, and the inventors of the present disclosure found two novel crystalline forms suitable for development after study.

Solubility is one of the key properties of drugs, which affects the absorption of drugs in human body directly. The solubility of different crystalline forms are remarkably different, and the absorption dynamics in vivo may also change, which results in different bioavailability and ultimately affects the clinical safety and efficacy of drugs.

Compared with Form A of the prior art, Form CS2 provided by the present disclosure has better solubility and dissolution rate, especially in FaSSIF (Fasted state simulated intestinal fluids), the solubility of Form CS2 is 43% higher than that of Form A of the prior art. The dissolution rate of Form CS2 is 5 times higher than that of Form A of the prior art, which generates unexpected effects. The solubility of Form A of the prior art in water is only 0.061 mg/mL, while Form CS1 provided by the present disclosure has superior solubility in water, and the solubility of Form CS1 in water is 16 times higher than that of Form A of the prior art, which generates unexpected effects. An increase in solubility is conducive to increase the bioavailability of drugs, thereby increasing the possibility of a successful drug product. In addition, the increase in solubility also reduces the difficulty of formulation process. For crystalline forms with sufficiently high solubility, the formulation processes can be developed using a conventional method, while for less soluble crystalline forms, more complex formulation processes are required to achieve the desired bioavailability. Moreover, the drug dose reduction without affecting efficacy is possible due to higher solubility, thereby reducing the side effects and improving the safety of drugs.

In addition, Form CS2 provided by the present disclosure has good stability, low hygroscopicity, high purity, uniform particle size. The crystalline form of Form CS2 doesn't change after being stored at 25° C./60% RH for three months, which makes Form CS2 suitable for preparation process and long-term storage.

Therefore, the discovery of Form CS1 and Form CS2 provides a better choice for the development of pharmaceutical compositions of AP26113, and is of great significance for the drug development of AP26113.

DETAILED DESCRIPTION OF THE DISCLOSURE

The present disclosure is further illustrated by the following examples which describe the preparation and uses of the crystalline forms of the present disclosure in detail. It is obvious to those skilled in the art that many changes in the materials and methods can be accomplished without departing from the scope of the disclosure.

The abbreviations used in the present disclosure are explained as follows:

XRPD: X-ray Powder Diffraction
DSC: Differential Scanning calorimetry
TGA: Thermal Gravimetric Analysis
DVS: Dynamic Vapor Sorption
HPLC: High Performance Liquid Chromatography
PLM: Polarized Light Microscopy
RH: Relative Humidity X-ray powder diffraction pattern in the present disclosure was acquired by a Panalytical Empyrean X-ray powder diffractometer. The parameters of the X-ray powder diffraction method of the present disclosure were as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present disclosure were acquired by a TA Q2000. The parameters of the differential scanning calorimetry (DSC) method of the present disclosure were as follows:

Heating rate: 10° C./min
Purge gas: nitrogen

Thermal gravimetric analysis (TGA) data in the present disclosure were acquired by a TA Q5000. The parameters of the thermal gravimetric analysis (TGA) method of the present disclosure were as follow:

Heating rate: 10° C./min
Purge gas: nitrogen
The dissolution data were collected on an Agilent 708-DS.
High Performance Liquid Chromatography (HPLC) data in the present disclosure are collected from an Agilent 1260 with a VWD detector.
The HPLC method parameters for purity test in the present disclosure are as follows:

1. Column: L021 Infinity lab Proshell 120EC-C18 50×3.0 mm, 2.7 μm
2. Mobile Phase: A: 25 mM $KH_2PO_4$
   B: Acetonitrile
   Gradient:

| Time (min) | % B |
|---|---|
| 0.0 | 20 |
| 5.0 | 40 |
| 7.0 | 80 |
| 8.0 | 80 |
| 8.1 | 20 |
| 12.0 | 20 |

3. Flow rate: 0.6 mL/min
4. Injection Volume: 2 μL
5. Detection wavelength: 210 nm
6. Column Temperature: 40° C.
7. Diluent: Acetonitrile/$H_2O$ (v/v, 1/1)

Unless otherwise specified, the following examples were operated at room temperature.

In the following examples, the AP26113 starting material is Form A reported in WO2016065028A1, but the starting crystalline form is not a limiting condition for preparing the crystalline forms of the present disclosure.

Example 1 Preparation of Form CS1

12.5 mg of AP26113 free base was dissolved in 0.5 mL of a solvent mixture of isopropanol and toluene (1:4, v/v). After filtering, the filtrate was covered with perforated parafilm and then evaporated at 50° C. for 2 days.

Figure 1:
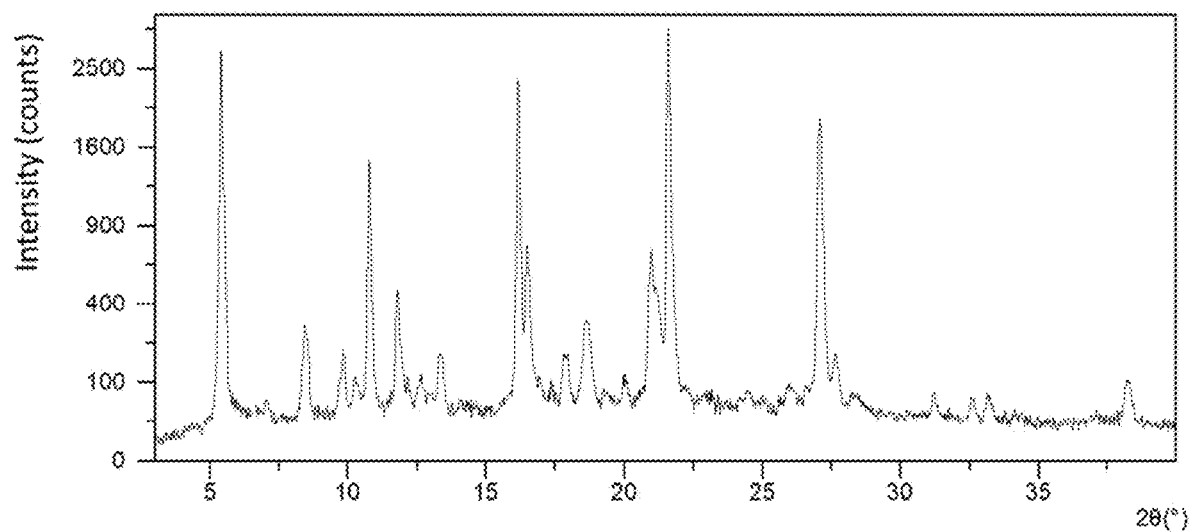
FIG. 1 shows an XRPD pattern of Form CS1 according to example 1.

The obtained solid is confirmed to be Form CS1 by XRPD, of which the XRPD pattern is substantially as depicted in FIG. 1, and the XRPD data are listed in Table 1.

Figure 2:
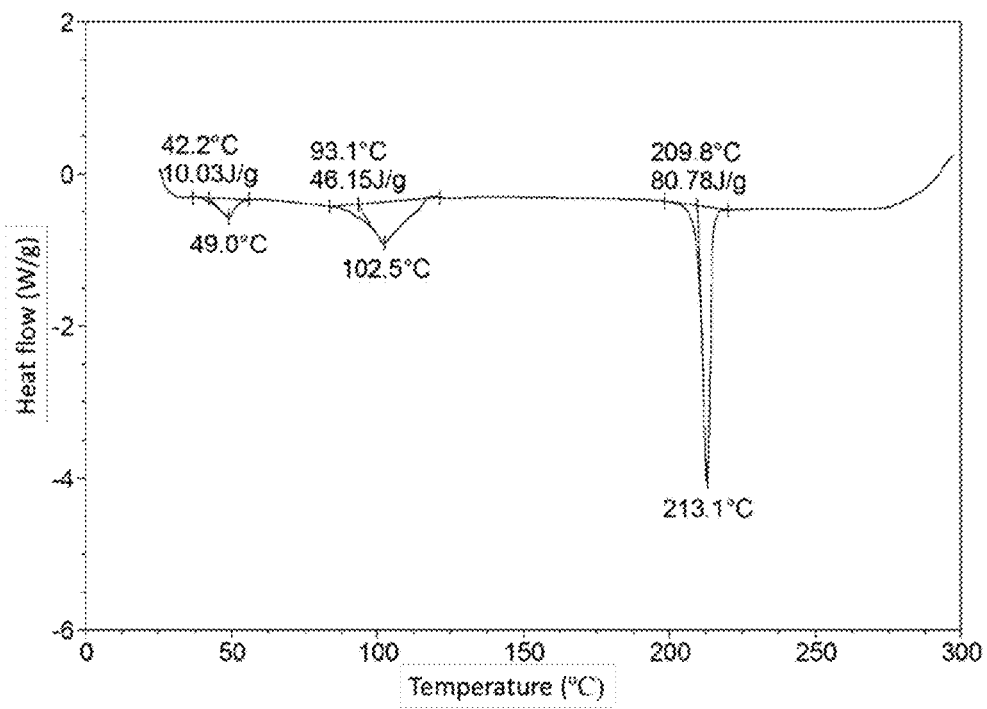
FIG. 2 shows a DSC curve of Form CS1 according to example 1.

The DSC curve of Form CS1 is substantially as depicted in FIG. 2. When DSC is applied to Form CS1, The first endothermic peak appears at around 42° C., the second endothermic peak appears at around 93° C., and the third endothermic peak appears at around 210° C.

Figure 3:
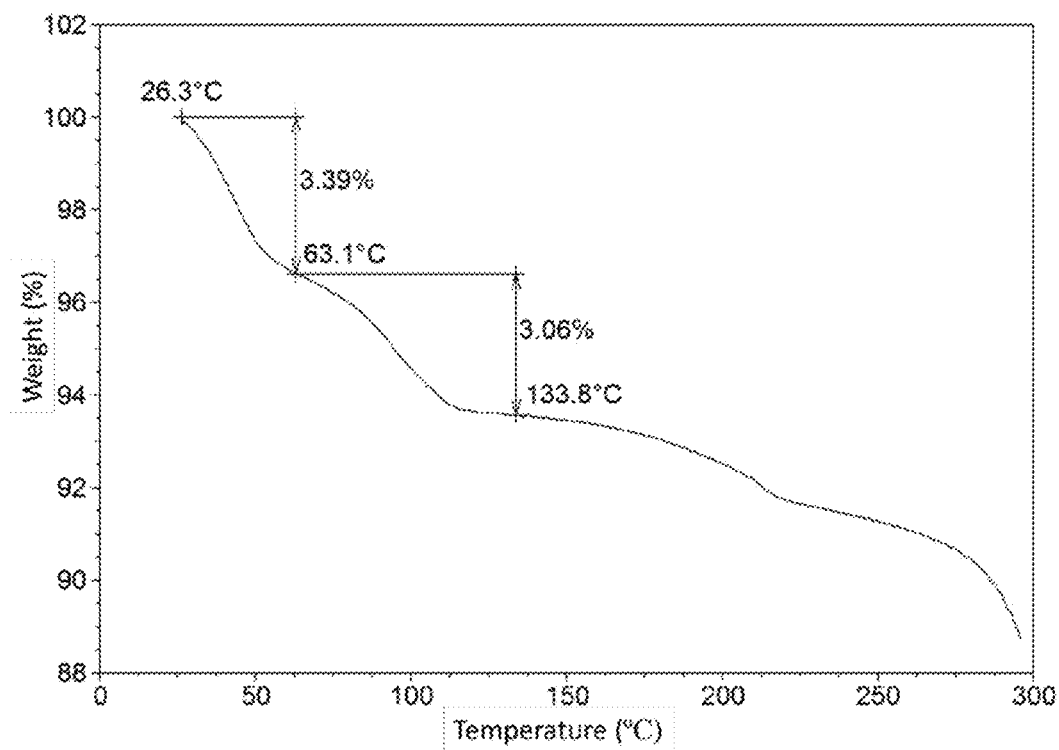
FIG. 3 shows a TGA curve of Form CS1 according to example 1.

The TGA curve of Form CS1 shows about 3.4% weight loss when heated to 63° C. and 3.1% weight loss when further heated to 134° C., which is substantially as depicted in FIG. 3.

TABLE 1

| 2θ | d spacing | Intensity % |
|---|---|---|
| 5.45 | 16.22 | 95.62 |
| 5.60 | 15.77 | 28.96 |
| 7.11 | 12.44 | 1.65 |
| 8.47 | 10.44 | 9.54 |
| 9.88 | 8.95 | 5.91 |
| 10.31 | 8.58 | 3.15 |
| 10.81 | 8.19 | 50.33 |
| 11.81 | 7.49 | 14.41 |
| 12.65 | 7.00 | 3.19 |
| 13.32 | 6.65 | 5.36 |
| 16.20 | 5.47 | 80.34 |
| 16.53 | 5.36 | 25.36 |
| 17.85 | 4.97 | 5.35 |

TABLE 1-continued

| 2θ | d spacing | Intensity % |
|---|---|---|
| 18.59 | 4.77 | 8.55 |
| 20.07 | 4.42 | 2.92 |
| 21.03 | 4.22 | 23.74 |
| 21.62 | 4.11 | 100.00 |
| 23.11 | 3.85 | 1.65 |
| 24.46 | 3.64 | 1.63 |
| 26.06 | 3.42 | 2.24 |
| 27.08 | 3.29 | 53.57 |
| 27.69 | 3.22 | 5.12 |
| 28.39 | 3.14 | 1.55 |
| 31.24 | 2.86 | 1.74 |
| 32.64 | 2.74 | 1.22 |
| 33.23 | 2.70 | 1.26 |
| 38.28 | 2.35 | 2.66 |

Example 2 Preparation of Form CS1

43.5 mg of AP26113 free base was dissolved in 2.0 mL of a solvent mixture of isopropanol and toluene (1:4, v/v). After filtering, the filtrate was evaporated at 35° C. for 10 days. The obtained solid is Form CS1, and the XRPD results are shown in Table 2.

TABLE 2

| 2θ | d spacing | Intensity % |
|---|---|---|
| 4.56 | 19.39 | 8.93 |
| 5.44 | 16.25 | 85.31 |
| 8.42 | 10.50 | 26.03 |
| 9.74 | 9.08 | 15.05 |
| 10.80 | 8.19 | 39.68 |
| 11.79 | 7.51 | 24.38 |
| 12.56 | 7.05 | 9.26 |
| 13.32 | 6.65 | 32.31 |
| 14.52 | 6.10 | 9.41 |
| 16.17 | 5.48 | 68.38 |
| 16.56 | 5.35 | 33.12 |
| 17.36 | 5.11 | 17.98 |
| 17.84 | 4.97 | 26.59 |
| 18.47 | 4.80 | 34.08 |
| 19.47 | 4.56 | 17.30 |
| 20.09 | 4.42 | 19.58 |
| 21.02 | 4.23 | 100.00 |
| 21.62 | 4.11 | 85.24 |
| 22.96 | 3.87 | 8.52 |
| 23.98 | 3.71 | 9.52 |
| 25.93 | 3.44 | 9.64 |
| 27.07 | 3.29 | 54.21 |
| 27.64 | 3.23 | 10.20 |
| 29.39 | 3.04 | 3.36 |
| 31.26 | 2.86 | 4.98 |
| 33.16 | 2.70 | 1.55 |
| 38.22 | 2.36 | 3.06 |

Example 3 Preparation of Form CS1

9.5 mg of AP26113 free base was dissolved in 0.6 mL of a solvent mixture of isopropanol and toluene (1:2, v/v). After filtering, the filtrate was evaporated at 50° C. for 6 days. The obtained solid is Form CS1, and the XRPD results are shown in Table 3.

TABLE 3

| 2θ | d spacing | Intensity % |
|---|---|---|
| 4.44 | 19.91 | 5.73 |
| 5.47 | 16.17 | 75.65 |

TABLE 3-continued

| 2θ | d spacing | Intensity % |
|---|---|---|
| 8.44 | 10.48 | 16.26 |
| 9.80 | 9.02 | 5.01 |
| 10.80 | 8.19 | 33.01 |
| 11.83 | 7.48 | 19.22 |
| 13.32 | 6.65 | 16.96 |
| 16.19 | 5.48 | 79.29 |
| 16.51 | 5.37 | 54.50 |
| 17.80 | 4.98 | 13.38 |
| 18.60 | 4.77 | 34.13 |
| 18.82 | 4.72 | 28.94 |
| 20.07 | 4.42 | 7.59 |
| 20.91 | 4.25 | 100.00 |
| 21.61 | 4.11 | 60.99 |
| 25.95 | 3.43 | 3.41 |
| 27.13 | 3.29 | 42.70 |
| 28.51 | 3.13 | 5.27 |
| 31.21 | 2.87 | 5.82 |

Example 4 Preparation of Form CS1

1.3 g of AP26113 free base was dissolved in 5.0 mL of a solvent mixture of ethanol and toluene (1:4, v/v) at 60° C. After filtering, the filtrate was sealed and stirred at −20° C. until solid precipitated. The obtained solid is Form CS1, and the XRPD results are shown in Table 4.

TABLE 4

| 2θ | d spacing | Intensity % |
|---|---|---|
| 5.44 | 16.25 | 100.00 |
| 8.45 | 10.47 | 11.68 |
| 9.76 | 9.07 | 2.98 |
| 10.28 | 8.60 | 3.34 |
| 10.82 | 8.18 | 16.22 |
| 11.79 | 7.51 | 13.87 |
| 12.23 | 7.24 | 4.85 |
| 13.27 | 6.67 | 10.26 |
| 14.13 | 6.27 | 1.60 |
| 16.16 | 5.48 | 35.67 |
| 16.55 | 5.36 | 23.48 |
| 17.86 | 4.97 | 8.93 |
| 18.64 | 4.76 | 31.22 |
| 20.02 | 4.44 | 7.10 |
| 20.86 | 4.26 | 51.39 |
| 21.63 | 4.11 | 30.45 |
| 23.12 | 3.85 | 3.26 |
| 24.48 | 3.64 | 5.64 |
| 26.07 | 3.42 | 5.86 |
| 27.24 | 3.27 | 31.51 |

Example 5 Preparation of Form CS1

At 50° C., 99.5 mg of AP26113 free base was dissolved in 6.0 mL of toluene saturated with water. After filtering, the filtrate was sealed and stirred at −20° C. until solid precipitated. The obtained solid is Form CS1, and the XRPD results are shown in Table 5.

TABLE 5

| 2θ | d spacing | Intensity % |
|---|---|---|
| 5.44 | 16.24 | 100.00 |
| 8.41 | 10.51 | 6.81 |
| 10.73 | 8.24 | 15.17 |
| 11.80 | 7.50 | 13.68 |
| 13.36 | 6.63 | 7.03 |
| 16.23 | 5.46 | 31.64 |
| 16.55 | 5.36 | 22.16 |
| 17.87 | 4.96 | 5.72 |
| 18.72 | 4.74 | 16.06 |
| 20.17 | 4.40 | 7.12 |
| 20.88 | 4.26 | 38.70 |
| 21.65 | 4.10 | 27.43 |
| 24.59 | 3.62 | 2.37 |
| 27.22 | 3.28 | 39.58 |

Example 6 Preparation of Form CS1

207.5 mg of AP26113 free base was dissolved in 1.0 mL of a solvent mixture of methanol and toluene (1:9, v/v) at 50° C. After filtering, the filtrate was sealed and stirred at −5° C. until solid precipitated.

Figure 4:
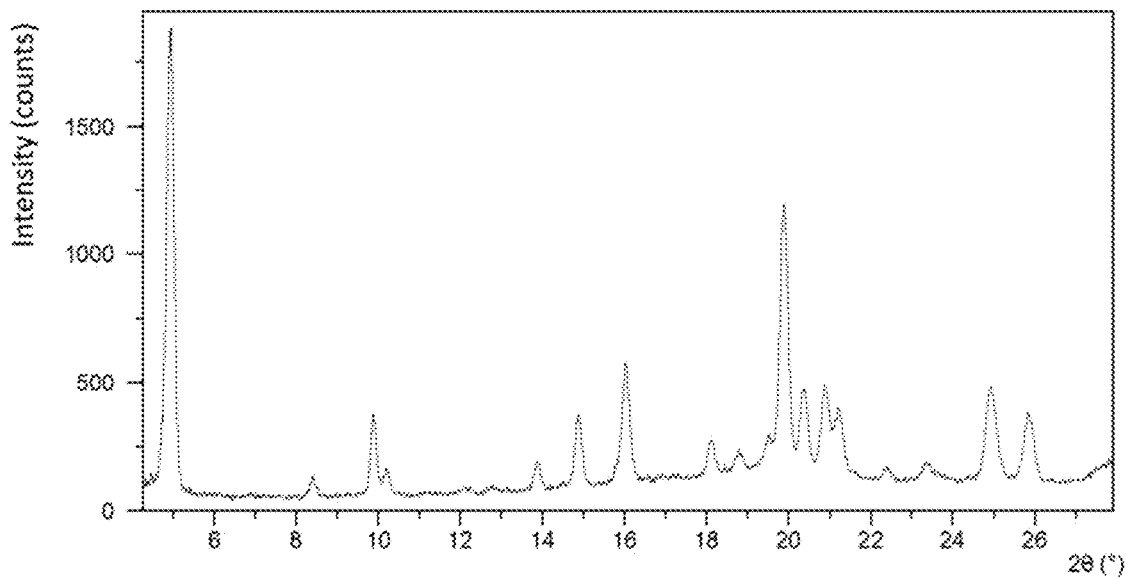
FIG. 4 shows an XRPD pattern of Form N1 according to example 6.

The obtained solid is Form N1 as characterized by XRPD, of which the XRPD results are shown in FIG. 4 and Table 6.

Form CS1 was obtained by drying N1. The XRPD results are shown in Table 7.

As depicted in FIG. 4, Form N1 shows characteristic peaks at 2theta values of 4.9°±0.2°, 9.8°±0.2°, 14.9°±0.2°, 16.0°±0.2°, 19.9°±0.2°, 24.9°±0.2° and 25.8°±0.2°.

TABLE 6

| 2θ | d spacing | Intensity % |
|---|---|---|
| 4.96 | 17.83 | 100.00 |
| 8.40 | 10.53 | 4.14 |
| 9.86 | 8.97 | 16.79 |
| 10.20 | 8.67 | 5.34 |
| 12.14 | 7.29 | 1.19 |
| 12.74 | 6.95 | 1.35 |
| 13.88 | 6.38 | 6.52 |
| 14.87 | 5.96 | 16.39 |
| 16.02 | 5.53 | 28.31 |
| 18.14 | 4.89 | 10.42 |
| 18.77 | 4.73 | 7.66 |
| 19.52 | 4.55 | 11.19 |
| 19.89 | 4.47 | 61.95 |
| 20.39 | 4.36 | 21.32 |
| 20.85 | 4.26 | 21.33 |
| 21.21 | 4.19 | 17.06 |
| 22.40 | 3.97 | 3.76 |
| 23.37 | 3.81 | 4.35 |
| 24.87 | 3.58 | 19.34 |
| 25.82 | 3.45 | 15.23 |

TABLE 7

| 2θ | d spacing | Intensity % |
|---|---|---|
| 5.44 | 16.25 | 100.00 |
| 6.92 | 12.77 | 0.90 |
| 8.45 | 10.47 | 21.99 |
| 9.79 | 9.03 | 5.70 |
| 10.32 | 8.57 | 4.40 |
| 10.82 | 8.18 | 16.24 |
| 11.84 | 7.47 | 16.54 |
| 12.19 | 7.26 | 7.14 |
| 12.61 | 7.02 | 6.70 |
| 13.29 | 6.66 | 18.08 |
| 14.23 | 6.23 | 2.14 |
| 16.21 | 5.47 | 47.45 |
| 16.54 | 5.36 | 31.64 |
| 16.79 | 5.28 | 15.68 |
| 17.43 | 5.09 | 5.67 |
| 17.83 | 4.97 | 14.54 |
| 18.72 | 4.74 | 45.91 |

TABLE 7-continued

| 2θ | d spacing | Intensity % |
|---|---|---|
| 19.34 | 4.59 | 6.66 |
| 20.03 | 4.43 | 13.12 |
| 20.90 | 4.25 | 76.00 |
| 21.34 | 4.16 | 45.23 |
| 21.66 | 4.10 | 42.50 |
| 23.14 | 3.84 | 6.28 |
| 24.53 | 3.63 | 9.90 |
| 26.06 | 3.42 | 9.77 |
| 27.17 | 3.28 | 53.81 |

Example 7 Preparation of Form CS2

Figure 5:
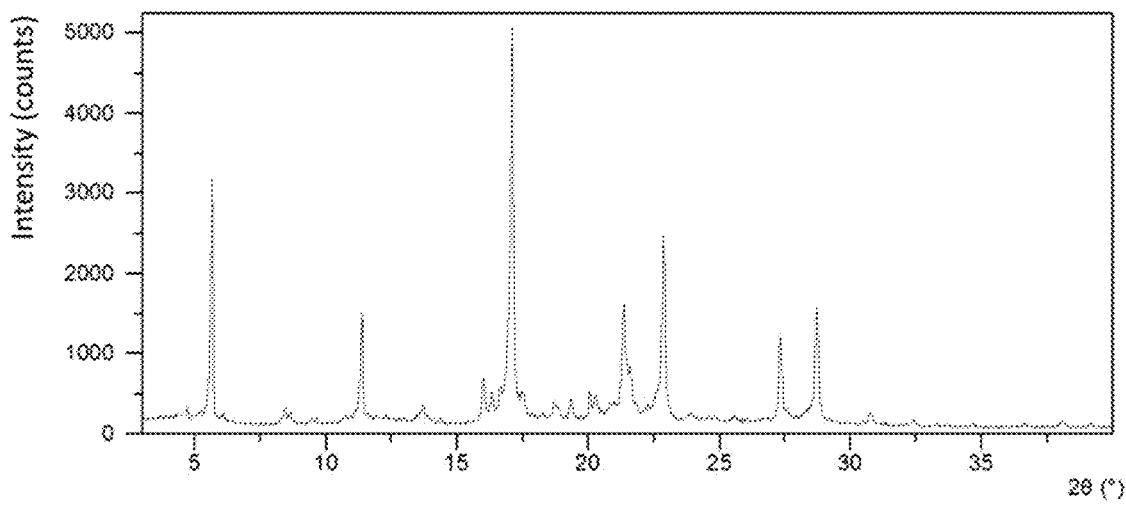
FIG. 5 shows an XRPD pattern of Form CS2 according to example 7.

10.0 mg of AP26113 free base was dissolved in 0.5 mL of a solvent mixture of isopropanol and toluene (1:4, v/v). After filtering, the filtrate was evaporated at 50° C. for 2 days. The obtained powder was kept at RT (relative humidity of environment between 50% RH and 80% RH) for 8 days to get Form CS2. The XRPD results of Form CS2 are shown in FIG. 5 and Table 8.

Figure 6:
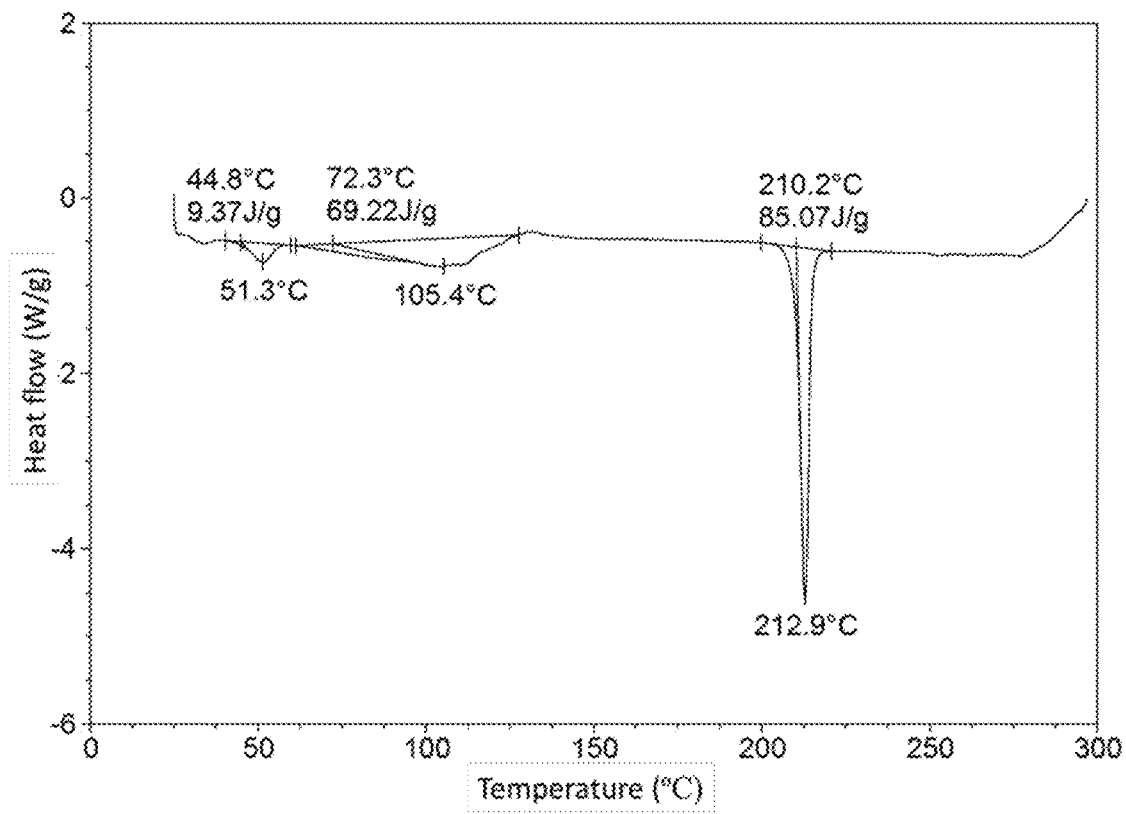
FIG. 6 shows a DSC curve of Form CS2 according to example 7.

The DSC curve of Form CS2 is depicted in FIG. 6, which shows three endothermic peaks. The first endothermic peak is around 45° C., the second endothermic peak is around 72° C., and the third endothermic peak is around 210° C.

Figure 7:
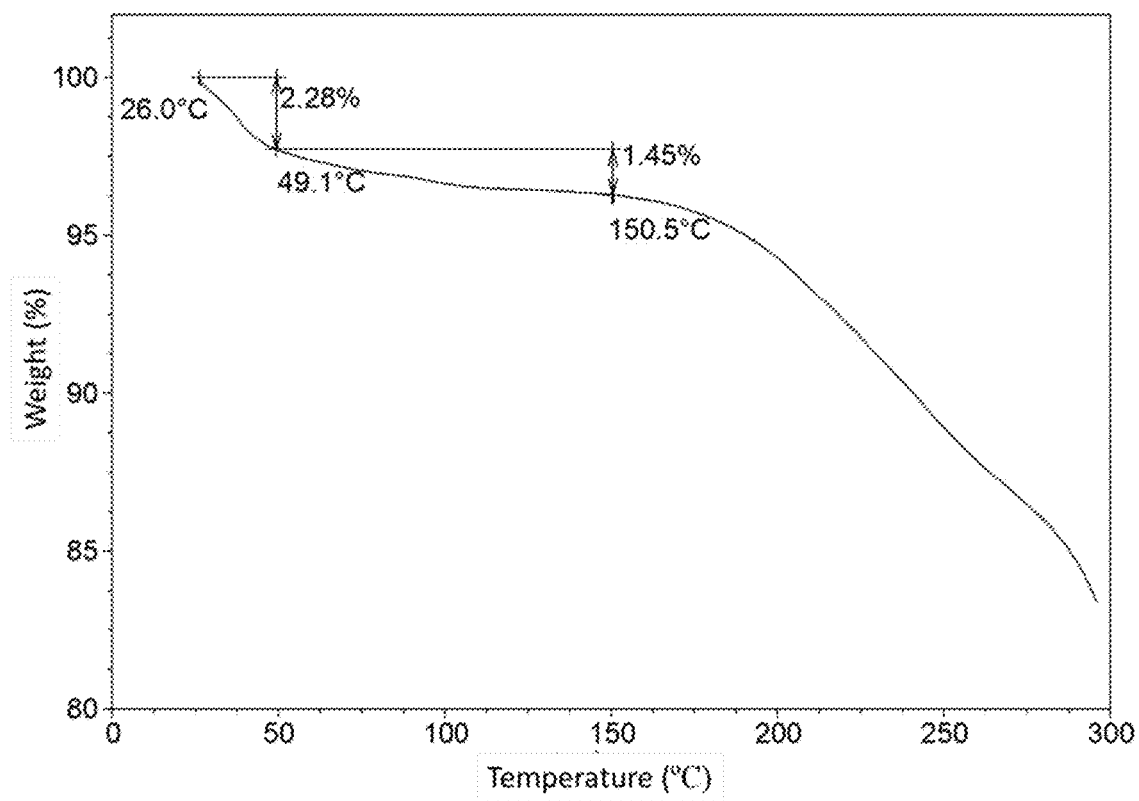
FIG. 7 shows a TGA curve of Form CS2 according to example 7.

The TGA curve of Form CS2 shows about 2.3% weight loss when heated to 49° C. and 1.5% weight loss when further heated to 151° C., which is depicted in FIG. 7.

TABLE 8

| 2θ | d spacing | Intensity % |
|---|---|---|
| 4.74 | 18.63 | 3.79 |
| 5.69 | 15.53 | 61.71 |
| 8.46 | 10.45 | 4.10 |
| 8.67 | 10.20 | 3.12 |
| 9.56 | 9.25 | 0.76 |
| 11.39 | 7.77 | 28.05 |
| 13.72 | 6.45 | 4.68 |
| 16.01 | 5.54 | 12.37 |
| 16.34 | 5.43 | 8.02 |
| 16.65 | 5.32 | 9.66 |
| 17.12 | 5.18 | 100.00 |
| 17.55 | 5.05 | 7.94 |
| 18.70 | 4.74 | 5.80 |
| 19.36 | 4.58 | 6.42 |
| 20.07 | 4.42 | 8.60 |
| 20.31 | 4.37 | 6.84 |
| 21.37 | 4.16 | 30.59 |
| 21.63 | 4.11 | 14.29 |
| 22.89 | 3.89 | 47.93 |
| 23.92 | 3.72 | 2.89 |
| 25.56 | 3.49 | 2.19 |
| 27.33 | 3.26 | 22.28 |
| 28.72 | 3.11 | 29.29 |
| 30.76 | 2.91 | 3.03 |
| 32.37 | 2.77 | 1.54 |
| 38.06 | 2.36 | 1.15 |

Example 8 Preparation of Form CS2

Figure 8:
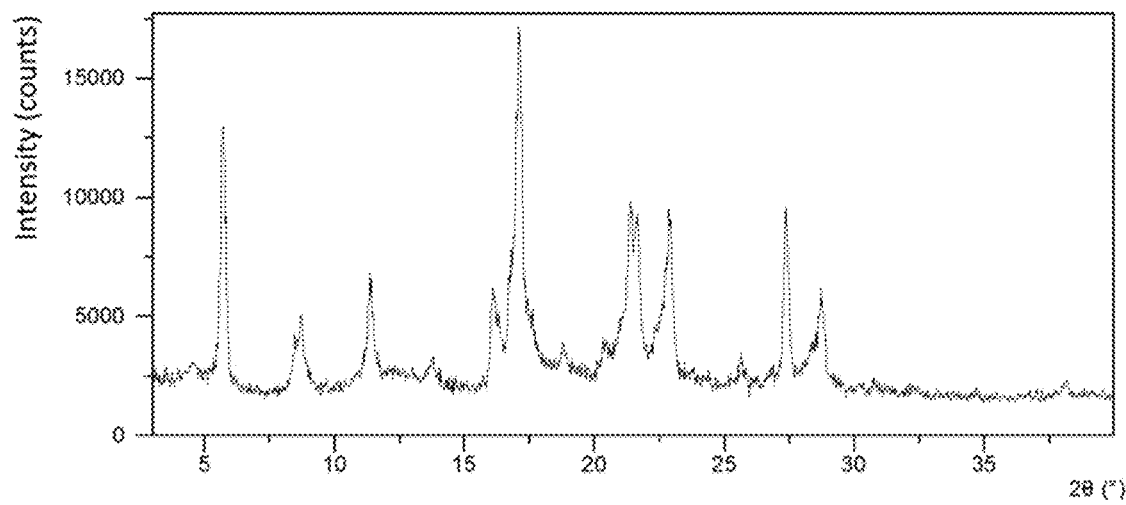
FIG. 8 shows an XRPD pattern of Form CS2 according to example 8.

38.0 mg of AP26113 free base was dissolved in 2.0 mL of a solvent mixture of isopropanol and toluene (1:4, v/v). After filtering, the filtrate was evaporated at 50° C. for 3 days. The obtained solid was kept under 57.6% RH at RT for 12 days to get Form CS2. And the XRPD results are shown in FIG. 8 and Table 9.

TABLE 9

| 2θ | d spacing | Intensity % |
|---|---|---|
| 4.51 | 19.61 | 4.96 |
| 5.69 | 15.54 | 70.28 |
| 8.72 | 10.14 | 21.62 |
| 11.38 | 7.77 | 30.53 |
| 13.73 | 6.45 | 8.64 |
| 16.08 | 5.51 | 27.38 |
| 17.13 | 5.18 | 100.00 |
| 18.82 | 4.72 | 12.30 |
| 20.40 | 4.35 | 12.90 |
| 21.38 | 4.16 | 52.38 |
| 21.68 | 4.10 | 46.61 |
| 22.94 | 3.88 | 49.09 |
| 25.69 | 3.47 | 6.99 |
| 27.36 | 3.26 | 49.47 |
| 28.73 | 3.11 | 25.41 |
| 38.12 | 2.36 | 3.58 |

Example 9 Preparation of Form CS2

Figure 9:
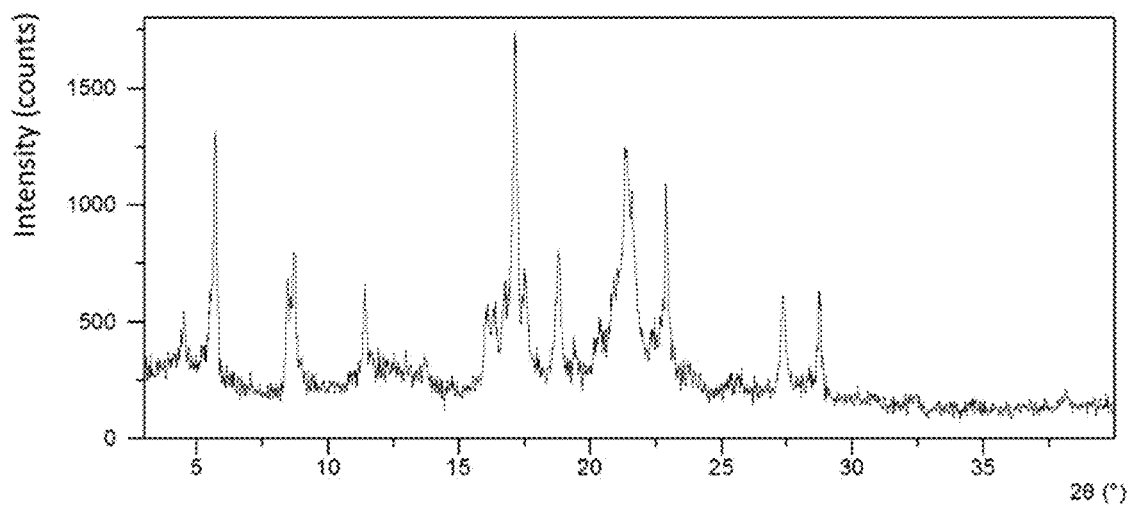
FIG. 9 shows an XRPD pattern of Form CS2 according to example 9.

About 10 mg of Form CS1 was kept under 57.6% RH at RT for 16 days to get Form CS2. And the XRPD results are shown in FIG. 9 and Table 10.

TABLE 10

| 2θ | d spacing | Intensity % |
|---|---|---|
| 4.50 | 19.66 | 16.38 |
| 5.74 | 15.40 | 73.60 |
| 8.46 | 10.46 | 30.33 |
| 8.74 | 10.12 | 40.47 |
| 11.41 | 7.76 | 25.37 |
| 16.05 | 5.52 | 22.74 |
| 17.14 | 5.17 | 100.00 |
| 17.52 | 5.06 | 34.37 |
| 18.80 | 4.72 | 42.02 |
| 21.39 | 4.15 | 72.32 |
| 22.88 | 3.89 | 53.06 |
| 27.37 | 3.26 | 27.67 |
| 28.73 | 3.11 | 31.37 |

Example 10 Preparation of Form CS2

Figure 10:
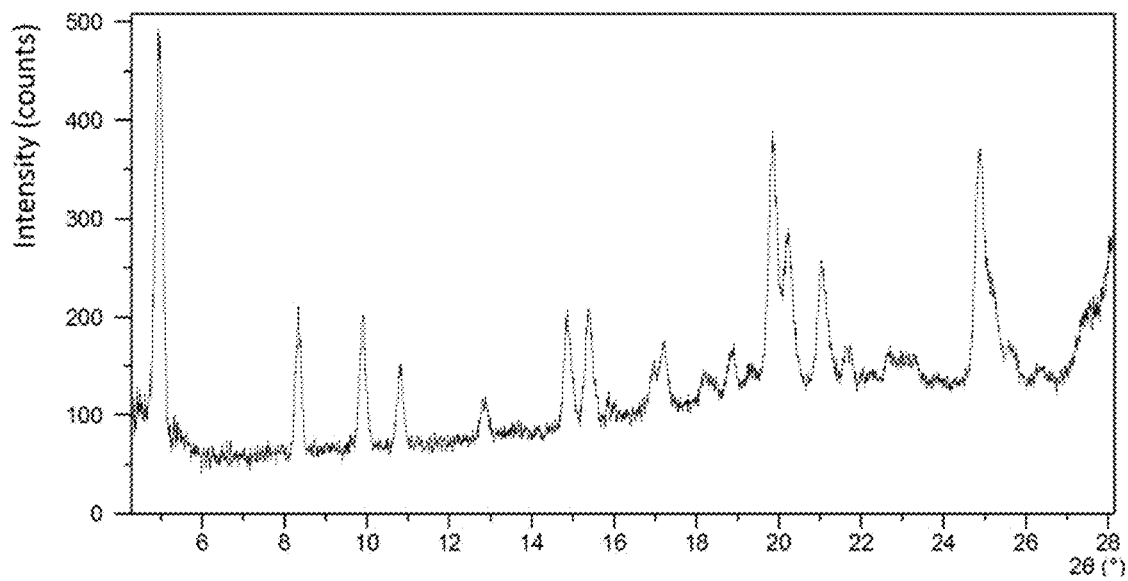
FIG. 10 shows an XRPD pattern of Form N3 according to example 10.
Figure 11:
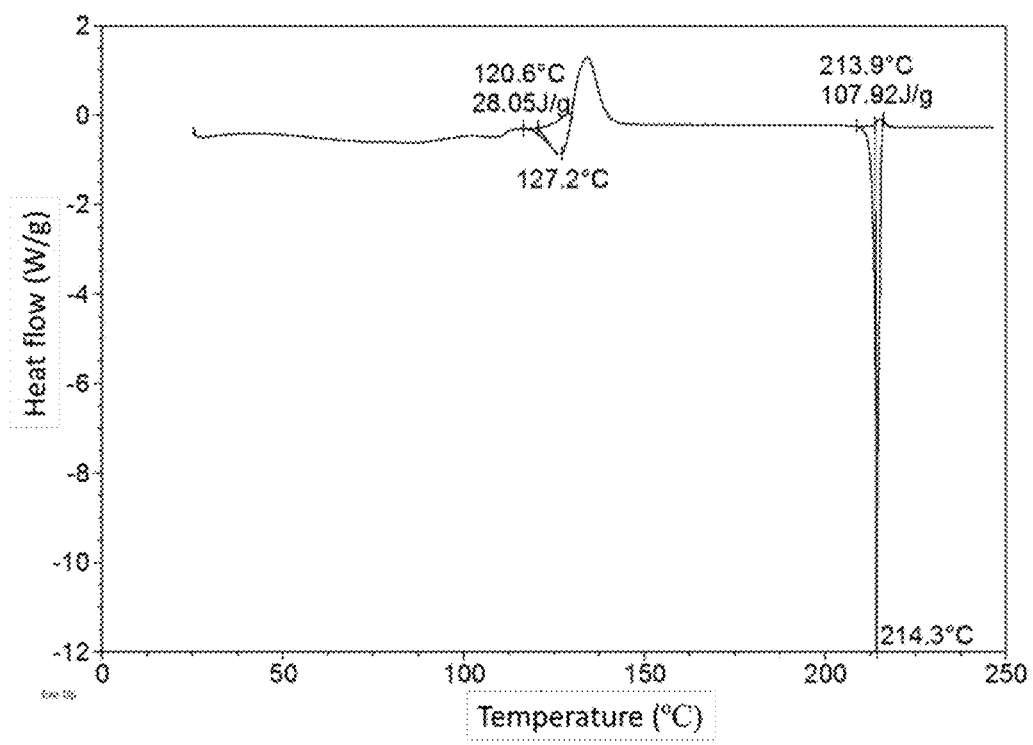
FIG. 11 shows a DSC curve of Form CS2 according to example 10.

1.8 g of AP26113 free base was dissolved in 5.0 mL of a solvent mixture of methanol and water (98:2, v/v). After filtering, the filtrate was sealed and stirred at −20° C. until solid precipitated. The obtained wet sample is Form N3 as characterized by XRPD, of which the XRPD results are shown in FIG. 10 and Table 11. Form CS2 was obtained by drying N3 under 40% RH at 35° C. The XRPD results are shown in Table 12. The DSC curve of Form CS2 is depicted in FIG. 11, which shows two endothermic peaks. The first endothermic peak is around 121° C., and the second endothermic peak is around 214° C.

Figure 12:
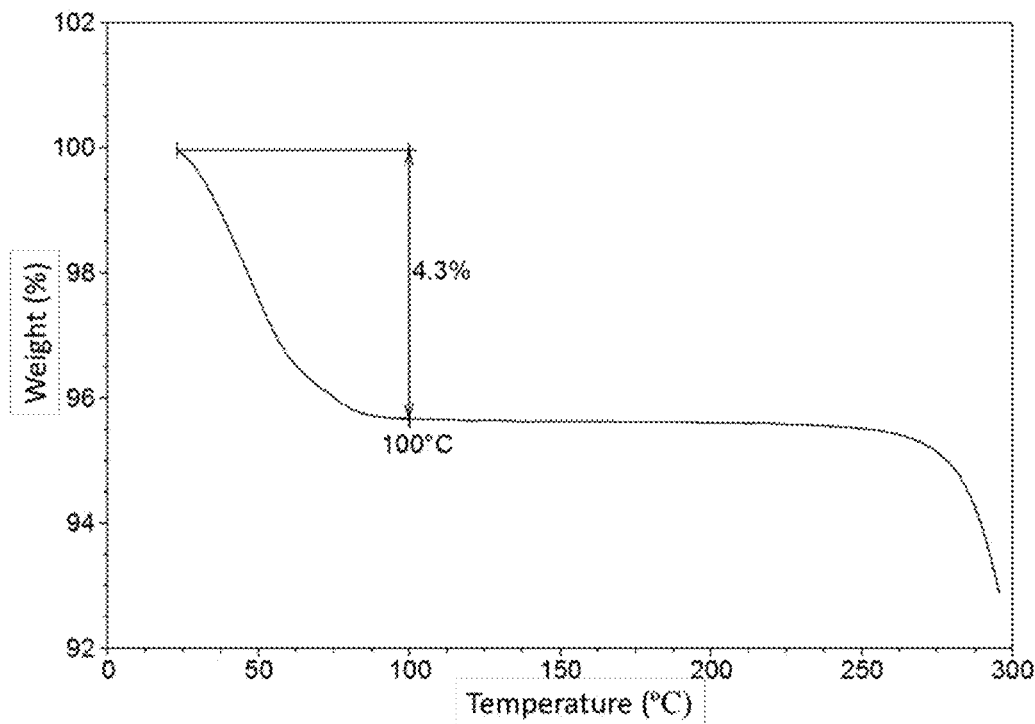
FIG. 12 shows a TGA curve of Form CS2 according to example 10.

The TGA curve of Form CS2 shows about 4.3% weight loss when heated to 100° C., which is depicted in FIG. 12.

As depicted in FIG. 10, Form N3 shows characteristic peaks at 2theta values of 4.9°±0.2°, 8.3°±0.2°, 9.9°±0.2°, 14.8°±0.2°, 15.4°±0.2°, 19.8°±0.2°, 21.0°±0.2° and 24.8°±0.2°.

Form CS2 could also be obtained in the above steps with volume ratio of methanol to water ratio changed to 93:7.

TABLE 11

| 2θ | d spacing | Intensity % |
|---|---|---|
| 4.92 | 17.97 | 100.00 |
| 8.35 | 10.59 | 35.51 |
| 9.89 | 8.94 | 35.54 |
| 10.81 | 8.18 | 21.78 |
| 12.85 | 6.89 | 13.59 |
| 14.85 | 5.97 | 34.52 |
| 15.37 | 5.76 | 37.07 |
| 17.21 | 5.15 | 28.22 |
| 18.25 | 4.86 | 20.40 |
| 18.89 | 4.70 | 26.28 |
| 19.84 | 4.47 | 81.32 |
| 20.22 | 4.39 | 55.98 |
| 21.04 | 4.22 | 49.84 |
| 21.68 | 4.10 | 26.36 |
| 22.99 | 3.87 | 24.35 |
| 24.83 | 3.59 | 70.55 |
| 27.40 | 3.26 | 34.83 |

TABLE 12

| 2θ | d spacing | Intensity % |
|---|---|---|
| 5.91 | 14.96 | 47.44 |
| 8.57 | 10.32 | 19.19 |
| 8.83 | 10.01 | 19.50 |
| 11.46 | 7.72 | 26.64 |
| 12.39 | 7.14 | 7.23 |
| 13.07 | 6.77 | 7.66 |
| 13.76 | 6.44 | 17.20 |
| 16.09 | 5.51 | 35.73 |
| 17.12 | 5.18 | 100.00 |
| 17.65 | 5.02 | 38.85 |
| 18.87 | 4.70 | 22.25 |
| 19.53 | 4.55 | 13.19 |
| 20.28 | 4.38 | 21.00 |
| 21.39 | 4.15 | 70.00 |
| 21.70 | 4.09 | 59.71 |
| 22.94 | 3.88 | 53.81 |
| 25.71 | 3.46 | 8.80 |
| 27.33 | 3.26 | 34.46 |
| 28.79 | 3.10 | 31.99 |
| 30.83 | 2.90 | 7.90 |
| 32.30 | 2.77 | 3.61 |
| 38.27 | 2.35 | 2.91 |

Example 11: Stability Study of Form CS2

Stability is one of the important properties for evaluating whether a crystalline form is pharmaceutically acceptable. The stability of a crystalline form, especially good stability during the commercial stage, is crucial for the stability of drugs. Reducing the change in dissolution rate and bioavailability caused by crystalline transformation is important to ensuring drug efficacy and safety and preventing adverse effects.

Figure 13:
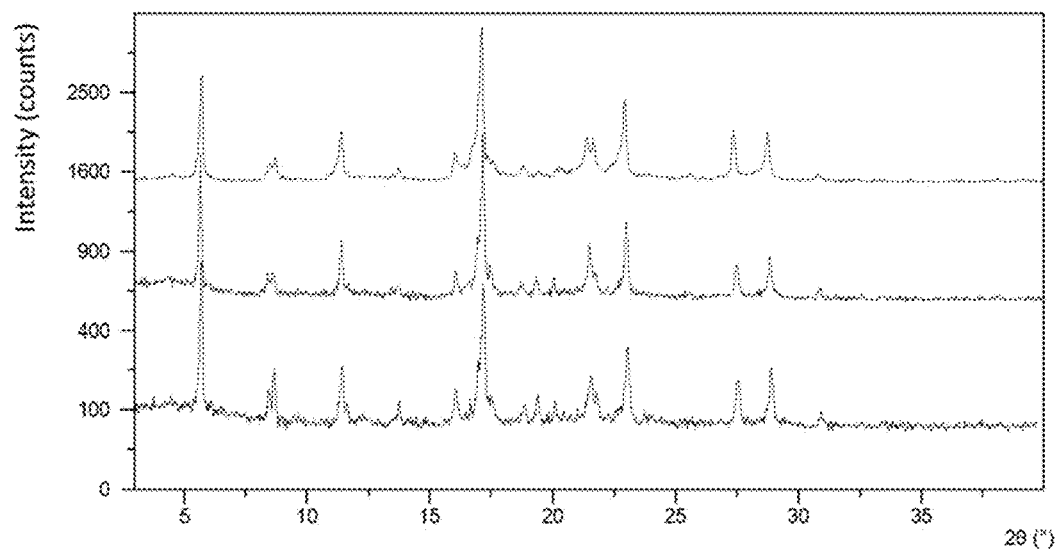
FIG. 13 shows an XRPD pattern overlay of Form CS2 before and after stored at 25° C./60% RH according to example 11 (From top to bottom: XRPD patterns of initial sample, after stored at 25° C./60% RH for 1 month, after stored at 25° C./60% RH for 3 months).

Approximately 10 mg of Form CS2 were stored in a temperature and humidity controlled chamber at 25° C./60% RH, and samples were taken for XRPD at the beginning and after stored for one month and three months. The results are as depicted in FIG. 13. It can be seen from the results that the crystalline form of Form CS2 doesn't change and the purity was all above 99%, indicating that Form CS2 has good stability and is suitable for drug development.

Example 12 Solubility Study

Solubility is one of the most important properties that affect bioavailability. In new drug discovery stage, new drug development stage and generic drug development stage. Improvement of solubility in bio-relevant media is of great significance for improving drug absorption and bioavailability.

Samples of Form CS2 of the present disclosure and Form A were suspended in FaSSIF (Fasted state simulated intestinal fluids) and SGF (Simulated gastric fluids) to get saturated solutions. The concentrations of the saturated solutions were measured by high performance liquid chromatography (HPLC) at fixed time points. The results are listed in Table 13.

TABLE 13

| | Solubility | | | |
|---|---|---|---|---|
| | FaSSIF | | SGF | |
| Time | Form CS2 (mg/mL) | Form A (mg/mL) | Form CS2 (mg/mL) | Form A (mg/mL) |
| 1 h | 9.9 | 6.9 | 11.2 | 10.9 |
| 4 h | 9.6 | 7.2 | 12.1 | 10.9 |

The results show that Form CS2 and Form A both have good solubility in SGF, while Form CS2 has a higher solubility than Form A in FaSSIF. The solubility of Form CS2 is 43% higher than that of Form A of the prior art in one hour, which generates unexpected effects. The intestinal tract is the main site of drug absorption. The significant improvement of solubility of Form CS2 in FaSSIF is beneficial to increase the absorption of drugs in gastrointestinal tract and enhance the bioavailability of AP26113.

Samples of Form CS1 of this present disclosure and Form A were suspended in $H_2O$ to get saturated solutions. After equilibrated for 1 h and 4 hours, the concentrations of the saturated solutions were measured by high performance liquid chromatography (HPLC). The results are listed in Table 14.

TABLE 14

| | Solubility $H_2O$ | |
|---|---|---|
| Time | Form CS1 (mg/mL) | Form A (mg/mL) |
| 1 h | 1.0 | 0.061 |
| 4 h | 0.61 | 0.067 |

The results show that the solubility of Form A is poor in water, which is disadvantageous for the absorption and bioavailability of drugs. The solubility of Form CS1 in water is 16 times higher than that of Form A of the prior art, which generates unexpected effects. The increased solubility of Form CS1 of the present disclosure is important for improving drug absorption and bioavailability.

Example 13 Dissolution Study 100 mg of Form CS2 and Form A were added into the die of intrinsic dissolution rate (IDR) tooling, and then compressed at 12 KN for 1 min. The dissolution of the intact tablets was tested using the following method and the results were listed in Table 15.

Dissolution medium: phosphate buffer (pH 6.8)
Dissolution method: rotating disk
Medium volume: 900 mL Revolving speed: 1000 rpm
Medium temperature: 37° C.

TABLE 15

| Time (min) | Cumulative dissolution (mg) | |
| --- | --- | --- |
| | Form CS2 | Form A |
| 10 | 6.4 | 0.6 |
| 15 | 8.0 | 0.9 |
| 20 | 9.4 | 1.1 |
| 25 | 10.7 | 1.4 |
| 30 | 11.8 | 1.6 |

Figure 14:
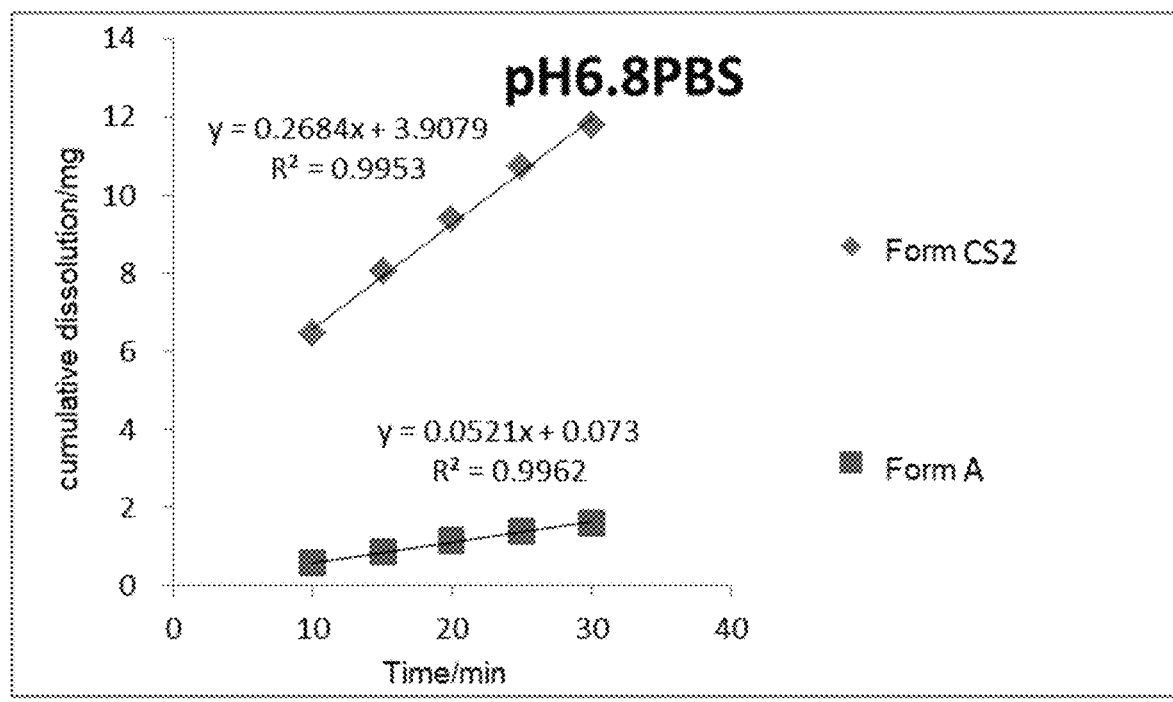
FIG. 14 shows dissolution curves of Form CS2 and Form A of the prior art according to example 13.

The results show that the cumulative dissolution of Form CS2 is remarkably higher than that of Form A at 10 min-30 min. By linearly fitting the cumulative dissolution with time, as shown in FIG. 14, the intrinsic dissolution rates of Form CS2 and Form A are 0.268 mg/min and 0.052 mg/min. The improvement of dissolution rate of Form CS2 is of great significance for the research and development of AP26113. In the process of formulation development, the use of Form CS2 with a higher dissolution rate can accelerate the dissolution and absorption in vivo after the administration of drugs. By adjusting the packaging materials and pharmaceutical excipients, it is possible to control the fast release at specific positions, and improve the duration of action and bioavailability of drugs.

Example 14 Particle Size Study

Particle size distribution of Forms CS1 and Form CS2 of the present disclosure and Form A of the prior art are tested. The average particle size of Form A is 12.58 μm, which is too small to be isolated effectively in the crystallization process. The Average particle sizes of Forms CS1 and Form CS2 are 175.0 μm and 151.9 μm, which are much larger than that of Form A. Compared with Form A, Form CS1 and Form CS2 with large particle size have less electrostatic attraction and can be separated more easily during the crystallization process. Moreover, the mixing non uniformity in the preparation process can be avoided, the quality of the drug is more controllable. At the same time, the crystal growth of the large particle size crystals is more perfect, and the adsorption of the solvent or the impurity on the crystals can be avoided, which is more helpful for purification.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A crystalline form CS2 of brigatinib, wherein the X-ray powder diffraction pattern shows characteristic peaks at 2theta values of 17.1°±0.2°, 22.9°±0.2° and 28.7°±0.2° using CuKα radiation.

2. The crystalline form CS2 according to claim 1, wherein the X-ray powder diffraction pattern shows 1 or 2 or 3 characteristic peaks at 2theta values of 27.3°±0.2°, 21.4°±0.2° and 5.7°±0.2° using CuKα radiation.

3. The crystalline form CS2 according to claim 1, wherein the X-ray powder diffraction pattern shows 1 or 2 or 3 characteristic peaks at 2theta values of 11.4°±0.2°, 8.7°±0.2° and 16.0°±0.2° using CuKα radiation.

4. A process for preparing crystalline form CS2 according to claim 1, wherein the process comprises:
   1) keeping the solid of crystalline form CS1 under 30% RH-80% RH at room temperature for 1-30 days to get Form CS2; or
   2) dissolving brigatinib free base in a solvent mixture of alcohols and water, filtering and then stirring the filtrate at a temperature between −20° C.-0° C. until solid precipitates, keeping the obtained wet cake under 30% RH-75% RH at 25° C.-40° C. to get crystalline form CS2.

5. The process for preparing crystalline form CS2 according to claim 4, wherein, in method 1): said humidity is 50% RH-80% RH; said keeping time is 5-16 days; in method 2): said alcohol is methanol; said volume ratio of alcohol and water is 93:7-98:2; said keeping temperature is 35° C., said keeping humidity is 40% RH.

6. A crystalline form CS1 of brigatinib, wherein the X-ray powder diffraction pattern shows characteristic peaks at 2theta values of 5.5°±0.2°, 21.6°±0.2° and 10.8°±0.2° using CuKα radiation.

7. The crystalline form CS1 according to claim 6, wherein the X-ray powder diffraction pattern shows 1 or 2 or 3 characteristic peaks at 2theta values of 16.2°±0.2°, 21.0°±0.2° and 27.1°±0.2° using CuKα radiation.

8. The crystalline form CS1 according to claim 6, wherein the X-ray powder diffraction pattern shows 1 or 2 or 3 characteristic peaks at 2theta values of 8.5°±0.2°, 11.8°±0.2° and 18.6°±0.2° using CuKα radiation.

9. A process for preparing crystalline form CS1 according to claim 6, wherein the process comprises:
   1) dissolving brigatinib free base in a solvent mixture of alcohols and aromatic hydrocarbons, and then evaporating the solution at 30° C.-60° C. for 1-10 days to obtain crystalline form CS1; or
   2) dissolving brigatinib free base in a solvent mixture of ethanol and aromatic hydrocarbons or a single solvent selected from aromatic hydrocarbons saturated with water, filtering and then stirring the filtrate at −20° C.-0° C. until solid precipitates, the obtained solid is crystalline form CS1; or
   3) dissolving brigatinib free base in a solvent mixture of methanol and aromatic hydrocarbons, filtering and then stirring the filtrate at −20° C.-0° C. until solid precipitates, drying the obtained wet cake to get Form CS1.

10. The process for preparing crystalline form CS1 according to claim 9, wherein, in method 1): said alcohol is isopropanol, said aromatic hydrocarbon is toluene, said volume ratio of alcohol and aromatic hydrocarbon is 1:4-1:2, said evaporation temperature is 35° C.-50° C.; in method 2): said aromatic hydrocarbon is toluene; said volume ratio of ethanol and aromatic hydrocarbon is 1:4, said water-saturated aromatic hydrocarbon is water-saturated toluene; in method 3): said aromatic hydrocarbon is toluene, said volume ratio of methanol and aromatic hydrocarbon is 1:9.

11. A pharmaceutical composition, wherein said pharmaceutical composition comprises a therapeutically effective amount of crystalline form CS2 according to claim 1, and pharmaceutically acceptable carriers, diluents or excipients.

12. A method of treating ALK positive non-small cell lung cancer, comprising administering to a patient in need thereof a therapeutically effective amount of CS2 according to claim 1.

13. A pharmaceutical composition, wherein said pharmaceutical composition comprises a therapeutically effective amount of crystalline form CS1 according to claim 6, and pharmaceutically acceptable carriers, diluents or excipients.

14. A method of treating ALK positive non-small cell lung cancer, comprising administering to a patient in need thereof a therapeutically effective amount of CS1 according to claim 6.

\* \* \* \* \*